United States Patent
Chow et al.

(10) Patent No.: US 10,076,496 B2
(45) Date of Patent: Sep. 18, 2018

(54) ENGINEERING OF POLYMER-STABILIZED NANOPARTICLES FOR DRUGS WITH LOG P VALUES BELOW 6 BY CONTROLLED ANTISOLVENT PRECIPITATION

(71) Applicant: THE CHINESE UNIVERSITY OF HONG KONG, Shatin (HK)

(72) Inventors: Albert Hee Lum Chow, Ma On Shan (HK); Shing Fung Chow, Yuen Long (HK); Xin Ran Zhang, Kunming (CN); Ka Yee Wan, Tsuen Wan (HK); Kwok Kin Cheng, Tsing Yi (HK); Lawrence William Baum, Ma On Shan (HK)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 0 days.

(21) Appl. No.: 13/673,810

(22) Filed: Nov. 9, 2012

(65) Prior Publication Data
US 2013/0122058 A1    May 16, 2013

Related U.S. Application Data

(60) Provisional application No. 61/558,906, filed on Nov. 11, 2011.

(51) Int. Cl.
| | |
|---|---|
| *A61K 9/14* | (2006.01) |
| *A61K 9/51* | (2006.01) |
| *B82Y 5/00* | (2011.01) |
| *A61K 47/40* | (2006.01) |
| *A61K 9/19* | (2006.01) |

(52) U.S. Cl.
CPC ............ *A61K 9/146* (2013.01); *A61K 9/5123* (2013.01); *A61K 9/5138* (2013.01); *A61K 9/5153* (2013.01); *A61K 9/5192* (2013.01); *A61K 9/19* (2013.01); *A61K 47/40* (2013.01); *B82Y 5/00* (2013.01)

(58) Field of Classification Search
CPC ....................................................... A61K 9/51
See application file for complete search history.

(56) References Cited

U.S. PATENT DOCUMENTS

| | | | | |
|---|---|---|---|---|
| 5,543,158 A | * | 8/1996 | Gref et al. ..................... | 424/501 |
| 5,817,334 A | * | 10/1998 | Schmidt et al. .............. | 424/450 |
| 2003/0170309 A1 | * | 9/2003 | Babcock .................. | A61K 9/08 |
| | | | | 424/486 |
| 2003/0181405 A1 | * | 9/2003 | Nordstrom ............ | A61K 38/212 |
| | | | | 514/44 R |
| 2003/0211162 A1 | * | 11/2003 | Kerkhof ........................ | 424/489 |
| 2005/0037083 A1 | * | 2/2005 | Brynjelsen et al. ........... | 424/489 |
| 2005/0238673 A1 | * | 10/2005 | Augustine et al. ............ | 424/400 |
| 2007/0148196 A1 | * | 6/2007 | Haas et al. ..................... | 424/401 |
| 2010/0203114 A1 | * | 8/2010 | Kwon et al. ................... | 424/450 |

OTHER PUBLICATIONS

Florence, Physiochemical Principles of Pharmacy, 5th edition, p. 175.*
D'Addio, S.M. "Novel Method for Concentrating and Drying Polymeric Nanoparticles: Hydrogen Bonding Coacervate Precipitation." Mol. Pharm. Feb. 22, 2010;7(2):557-564.†

\* cited by examiner
† cited by third party

*Primary Examiner* — Kyle A Purdy
(74) *Attorney, Agent, or Firm* — Kilpatrick Townsend & Stockton LLP

(57) ABSTRACT

The present invention provides organic nanoparticles that include a molecule having a Log P value of about 3 or above, an amphiphilic diblock copolymer or a surfactant, and a pharmaceutically-acceptable hydrophilic polymer. The present invention also provides methods of making these nanoparticles, e.g., by flash nanoprecipitation, with control over particle size and surface properties. The methods of the present invention provide a means for co-precipitating a water-insoluble compound with an amphiphilic stabilizer within a few milliseconds. The nanoparticles of the present invention exhibit high drug loading, e.g., 50% w/w, and can be produced with a mean particle size less than 200 nm and with a narrow particle size distribution.

28 Claims, 6 Drawing Sheets

ENGINEERING OF POLYMER-STABILIZED NANOPARTICLES FOR DRUGS WITH LOG P VALUES BELOW 6 BY CONTROLLED ANTISOLVENT PRECIPITATION

This patent application claims the benefit of U.S. Provisional Patent Application No. 61/558,906, filed Nov. 11, 2011, the contents of which are hereby incorporated herein by reference in the entirety.

BACKGROUND OF THE INVENTION

Drug-carriers and associated delivery methods are needed for certain drugs, which are only effective if delivered in a targeted fashion to a specific receptor site. Nanocarrier drug delivery systems, such as organic nanoparticles, offer several advantages when compared to conventional methods for delivering such drugs. Some of these potential advantages include an increased blood circulation time (Litzinger D C, et al., "Effect of liposome size on the circulation time and intraorgan distribution of amphipathic poly(ethylene glycol)-containing liposomes," 1994, *Biochim Biophys Acta, Biomembr* 1190:99-107), an enhanced ability to permeate cellular membranes, and an increased retention time at the targeted receptor site (Allen T M, et al., "Drug Delivery Systems: Entering the Mainstream," 2004, *Science* 303: 1818-1822; Duncan R, et al., "Drug targeting in cancer therapy: the magic bullet, what next?" *J Drug Targeting*, 1996, 3:317-319). Because the aforementioned advantages are dependent on the nanocarrier's physical dimensions and properties, it is important to control the size of the nanocarrier, often below 100 nm in diameter, as well as the nanocarrier's surface properties.

Flash nanoprecipitation (FNP) is a technique that has been used to produce organic nanoparticles containing drugs with a Log P greater than about 6, based on the anti-solvent precipitation principle and the use of amphiphilic diblock copolymers. FNP has been used to produce suspensions of these organic nanoparticles having an average diameter below 200 nm and containing hydrophobic compounds or drugs such as β-carotene (Log P=15.5); paclitaxel (Log P=7.38); and bifenthrin (Log P=6.0) (Zhu, Z., et al., "Formation of Block Copolymer-Protected Nanoparticles via Reactive Impingement Mixing", 2007, *Langmuir*, 23:10499-10504; also Saad, W. S., "Drug nanoparticle formation via flash nanoprecipitation: Conjugation to encapsulate and control the release of paclitaxel," Ph.D. Dissertation, Princeton University, 2007; also Liu, Y. et al., "Stabilized polymeric nanoparticles for controlled and efficient release of bifenthrin," 2008, *Pest Manage Sci*, 64:808-812). However, FNP has not been used to produce stable organic nanoparticles containing drugs that have a Log P less than about 6. Nanoparticles produced by FNP with drugs having a Log P lower than 6 were shown to be unstable towards aggregation and particle growth, i.e., Oswald ripening.

Accordingly, there is a need in the field, to which the present invention pertains, for stable organic nanoparticles that contain drugs having a Log P less than 6. Surprisingly, the present invention fulfills this as well as other related needs in the field.

BRIEF SUMMARY OF THE INVENTION

In one aspect, the present invention provides a nanoparticle having a spherical particle morphology and an average particle diameter of about 50 nm to about 200 nm. The nanoparticle includes a molecule having a Log P value of about 3 or above; an amphiphilic diblock copolymer or a surfactant; and a pharmaceutically-acceptable hydrophilic polymer. In certain aspects, the pharmaceutically-acceptable hydrophilic polymer is polyvinyl pyrrolidone (PVP), polyvinyl alcohol (PVA), or hydroxypropyl methylcellulose.

In a second aspect, the present invention provides a method of making a nanoparticle. The method includes these steps: (1) mixing in a mixer an organic solvent, an antisolvent, a molecule having a Log P value of about 3 or above, and a pharmaceutically-acceptable hydrophilic polymer with suspending properties selected from polyvinyl pyrrolidone, polyvinyl alcohol or hydroxypropyl methylcellulose; and (2) producing spherical nanoparticles having an average particle diameter of about 50 nm to about 200 nm by flash nanoprecipitation.

In a third aspect, the present invention provides a method of drying a nanoparticle to yield a solid powder. The method includes co-freeze drying the nanoparticle with a cryoprotectant. In certain aspects, the cryoprotectant is a sugar or a beta-cyclodextrin at a concentration of not more than 2% w/v.

In a fourth aspect, the present invention provides a method of delivering a molecule, which is a part of the nanoparticle described above. The method comprises administering to a subject an effective amount of the nanoparticles as set forth herein.

In a fifth aspect, the present invention provides a method set forth herein wherein the drug is present in a water-soluble salt form.

In a sixth aspect, the present invention provides a method set forth herein which optionally includes a neutralization step that includes using a base or an acid in the aqueous phase during the precipitation process.

DETAILED DESCRIPTION OF THE INVENTION

I. General

Figure 1:
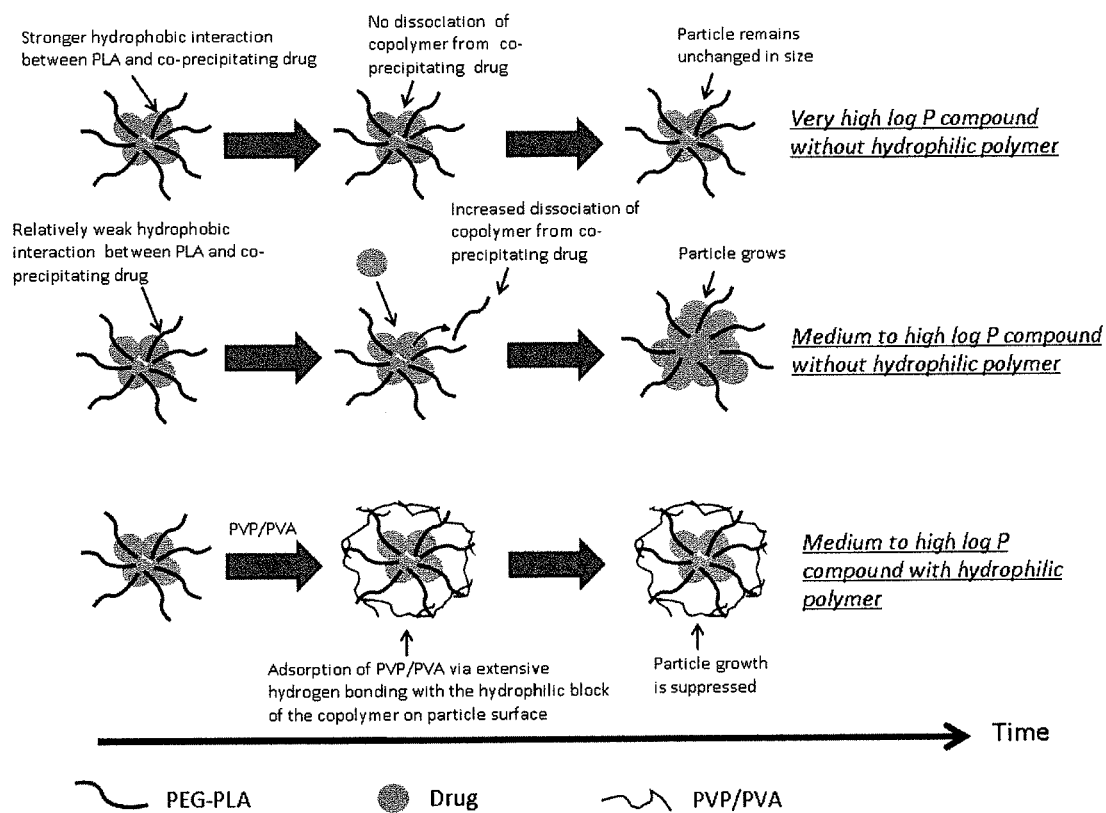
FIG. 1 shows a schematic diagram outlining a proposed stabilization mechanism of PVP/PVA for compounds as a function of Log P. As used herein, "medium log P" refers to a Log P value of about 0 to about 3; "high log P" refers to a Log P value of about 3 to about 4; "very high log P" refers to a Log P value of about 4 to about 7.

The present invention provides nanoparticles that include a molecule having a Log P value of about 3 or above, an amphiphilic diblock copolymer or a surfactant, and a pharmaceutically-acceptable hydrophilic polymer. The present invention also provides method of making these nanoparticles, e.g., by flash nanoprecipitation, with control over particle size and surface properties. The methods of the present invention provide a means for co-precipitating a water-insoluble compound with an amphiphilic stabilizer within a few milliseconds. The nanoparticles of the present invention exhibit high drug loading, e.g., greater than 5% w/w, and can be produced with a mean particle size less than 200 nm and with a narrow particle size distribution, e.g., polydispersity index of about 0.3 or less and a span of about 2 or less. Additionally, the present invention demonstrates that the incorporation of pharmaceutically-acceptable hydrophilic polymers stabilizes nanoparticles that include molecules having a Log P of about 3 or above.

II. Definitions

The terms "a," "an," or "the" as used herein not only include aspects with one member, but also aspects with more than one member. For example, an embodiment including " a nanoparticle" should be understood to include the presence of more than one nanoparticle.

The term "or" as used herein should in general be construed non-exclusively. For example, an embodiment of "a formulation including A or B" would typically present an aspect with a formulation including both A and B. "Or" should, however, be construed to exclude those aspects presented that cannot be combined without contradiction (e.g., a formulation pH that is between 9 and 10 or between 7 and 8).

The abbreviations used herein have their conventional meaning within the chemical, biological or pharmaceutical arts.

The terms "about" and "approximately equal" are used herein to modify a numerical value and indicate a defined range around that value. If "X" were the value, "about X" or "approximately equal to X" would generally indicate a value from 0.90X to 1.10X. Any reference to "about X" minimally indicates at least the values X, 0.90X, .91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

In formulations including an "additional," "further," or "second" component, the second component as used herein is chemically different from the other components or first component. A "third" component is different from the other, first, and second components, and further enumerated or "additional" components are similarly different.

As used herein, the term "nanoparticle" refers to a particle having physical dimensions on the nanoscale. For example, a nanoparticle includes a particle that is spherical and has an average diameter of approximately 1, 2, 3, 4, 5, 6, 7, 8, 9, 10, 15, 20, 25, 30, 40, 50, 60, 75, 100, 200, 300, 400, or 500 nm.

As used herein, the term "hydrophobic" refers to its plain ordinary meaning and refers to a chemical group having a tendency to attract non-polar or uncharged chemical groups, e.g. hexane, and to repel polar or charged chemical groups, e.g. water. "Hydrophobic" also refers to a chemical that tends not to dissolve in, mix with, or be wetted by water.

As used herein, the phrase "hydrophobic molecule" refers to any molecule having a greater tendency to be soluble in organic solvents as compared with aqueous solvents. A hydrophobic molecule includes, but is not limited to, one having a Log P of at least 0.2 or above. Some hydrophobic molecules suitable for use with the present invention include those molecules having a Log P of at least 1 or above. Some other hydrophobic molecules that are suitable for use with the present invention include those molecules having a Log P of at least 2 or above and also those molecules having a Log P of at least 3 or above.

As used herein, the term "hydrophilic" refers to its plain ordinary meaning and refers to a chemical group having a tendency to repel non-polar or uncharged chemical groups, e.g., hexane, and to attract polar or charged chemical groups, e.g., water. "Hydrophilic" also refers to a chemical that tends to dissolve in, mix with, or be wetted by water.

As used herein, the phrase "hydrophilic molecule" refers to any molecule having a greater tendency to be soluble in aqueous solvents as compared with organic solvents. A hydrophilic molecule includes, but is not limited to, one having a Log P of at least 0.2 or less.

As used herein, the term "Log P" refers to the mathematical resultant of the logarithmic base-10 function of the Partition Coefficient, P; wherein P is the relative ratio of the solubility of a compound in an organic phase relative to the solubility of the same compound in an aqueous phase. In other words, P is the ratio of the concentration of a compound in an organic phase, which is represented by "[Organic]," to the concentration of the same compound in an aqueous phase, which is represented by [Aqueous]". Mathematically, Log P=$\log_{10}$([Organic]/[Aqueous]). For example, Log P=1 when the ratio of the concentration of a compound in an organic phase to the concentration of the same compound in an aqueous phase is 10:1. Log P=0 when the ratio of the concentration of a compound in an organic phase to the concentration of the same compound in an aqueous phase is 1:10. Log P=−1 when the ratio of the concentration of a compound in an organic phase to the concentration of the same compound in an aqueous phase is 1:10. For drugs, the reference organic phase is n-octanol. Log P only considers the concentration of un-ionized solute compounds in both the organic and aqueous phases. As such, Log P is a value which reflects the intrinsic hydrophilic and hydrophobic nature of a compound or drug and is therefore independent of the pH of the solvent and the pKa of the compound.

As used herein the term "Log D" refers to the mathematical resultant of the logarithmic base-10 function of the Distribution Coefficient, D; wherein D is the relative ratio of the solubility of all species, both ionized and not ionized, in an organic phase relative to the solubility of the same species in an aqueous phase. In contrast to Log P, Log D considers ionized as well un-ionized species. As such, Log D is sensitive to pH and pKa of the compound of interest.

As used herein, the term "amphiphilic" refers to compounds that possess both hydrophilic and hydrophobic properties. Amphiphilic compounds typically have a water-soluble polar group, which is hydrophilic, and also have a water-insoluble non-polar group, which is hydrophobic. The portion of an amphiphilic compound that is the water-insoluble non-polar group is typically composed of organic chemical groups. Non-limiting examples of amphiphilic compounds include octyl alcohol and sodium stearate. Amphiphilic compounds are useful for preparing emulsions and for controlling the structure of liquid crystals. Non-limiting examples of amphiphilic compounds include ionic amphiphilic compounds such as phospholipids, sodium dodecyl sulfate, and benzalkonium chloride, and non-ionic amphiphilic compounds such as block copolymers composed of polyethylene and polypropylene blocks.

As used herein, the term "polymer" refers to a macromolecule formed by the chemical union of five or more identical combining units called monomers. The actual number of monomers comprising a polymer is typically quite large and often is not precisely known. Non-limiting examples of polymers include polyethylene oxide, polypropylene oxide, polyvinyl pyrrolidine, and polyvinyl alcohol.

As used herein, the phrase "block polymer" or "block copolymer" refers to a polymer that is comprised of alternating sections of one chemical composition separated by sections of a different chemical composition. For example, one of the alternating sections can be comprised of one type of monomer that is chemically bonded to other monomers of the same type and another of the alternating sections can be comprised of a different and second type of monomer that is chemically bonded to other monomers of the same type as the second type. Each alternative section of a particular type of monomer is referred to as a block. Polymers composed of two different alternating sections, i.e. blocks, are referred to as a "diblock polymers." Polymers composed of three different alternating sections, i.e. blocks, are referred to as a "triblock polymers." Block polymers can be composed of two, three, four, five, six, seven, eight, nine, ten, or more blocks.

As used here, the term "surfactant" and the phrase "surface-active agent" refers to any compound that reduces the surface tension when dissolved in water, water solutions, or other hydrophilic or polar solutions. Surfactants also refer to compounds that reduce that interfacial tension between two liquids or between a liquid and a solid. Surfactants include detergents, wetting agents, and emulsifiers.

As used herein, the term "pharmaceutically-acceptable" is used as equivalent to physiologically acceptable. The phrase "pharmaceutically acceptable polymer" refers to a polymer that is neither biologically nor otherwise undesirable, e.g., the polymer does not elicit an adverse biological effect. In certain embodiments, a pharmaceutically-acceptable composition or preparation will include agents for buffering and/or preservation in storage and can include buffers and carriers for appropriate delivery, depending on the route of administration. A "pharmaceutically-acceptable" polymer is a polymer that is acceptable for physiological applications. Non-limited examples of "pharmaceutically-acceptable" polymers include polyvinyl pyrrolidone, polyvinyl alcohol, and hydroxypropyl methylcellulose.

As used herein, the phrase "suspending properties" refers to the ability of a first substance, e.g., a polymer, to incorporate or to include a second substance, e.g., a drug, which is otherwise immiscible in the solvent of the first substance. For example, certain polymers such as polyvinyl pyrrolidone can incorporate and suspend a drug in an aqueous media, in which the drug would not be soluble or suspended in the absence of the polymer with suspending properties.

As used herein, the phrase "polyvinyl pyrrolidone" refers to a polymer, classified as CAS #9003-39-8, containing vinyl pyrrolidone monomeric units and having an average molecular weight between about 10,000 and 40,000 g/mol.

As used herein, the phrase "polyvinyl alcohol" refers to a polymer, classified as CAS #9002-89-5, containing ethanolic monomeric units and having an average molecular weight between about 30,000 and 200,000 g/mol.

As used herein, the phrase "hydroxypropyl methylcellulose" refers to a polymer, which is classified as CAS #9004-65-3.

As used herein, the term "lecithin" refer to compounds having the generic formula $C_8H_{17}O_5NRR'$, wherein R and R' are fatty acid groups. Pure lecithin refers a phosphatidyl choline. Lecithins also refer to mixtures of diglycerides of fatty acids linked to the choline ester of phosphoric acid. Commercial lecitin refers to a mixture of acetone-insoluble phosphatides.

As used herein, the term "cholesterol" refers to a steroid compound, classified as CAS #57-88-5, and having a molecular formula of $C_{27}H_{45}OH$. Cholesterol also refers to derivatives of naturally occurring cholesterol.

As used herein, the terms "D-α-Tocopherol" and "tocopherol" refer to methylated phenol derivatives which may have vitamin E activity. D-α-Tocopherol is classified as CAS #59-02-9 and has the empirical formula, $C_{29}H_{50}O_2$.

As used herein, the terms "polyethylene glycol" and "polyethylene glycol 1" refer to compounds which are classified as CAS #25322-68-3, including salts and known equivalents thereof. The number 1000 indicates the molecular weight of the polyethylene glycol.

As used herein, the term "polyethylene glycol 1000 succinate" refers to the succinate derivative of polyethylene glycol 1000. The number 1000 indicates the molecular weight of the polyethylene glycol.

As used herein, the term "D-αTocopherol polyethylene glycol 1000" refers to a compound classified as CAS #9002-96-4.

As used herein, the term "sugar" refers to a general class of carbohydrate compounds, many of which are the product of photosynthesis. Non-limiting examples of sugars, include but are not limited to, glucose, manose, sucrose, galactose, fructose. Also included in the definition of sugar are monosaccharides, disaccharides, and polysaccharides.

As used herein, the terms "beta-cyclodextrin" and "cyclodextrins" refer to a large cyclic organic compound composed of sugar molecules. Cyclodextrins are characterized by the ability to increase the solubility of hydrophobic compounds, e.g. testosterone, in hydrophilic solvents, e.g., water.

As used here, the phrase "% loading" or "percent loading" refers to the amount of a molecule, which is included in the nanoparticle, relative the amount of nanoparticle. "% loading" and "percent loading" are often and equivalently expressed as weight percent or also % w/w. For example, a nanoparticle that includes a molecule at 80% loading refers to a nanoparticle having a molecule included that accounts for 80% of the weight of the nanoparticle.

As used herein, the phrase "biodegradable polymer" refers to a polymer that is susceptible to decomposition by microorganisms, bacteria, and/or in the natural environment.

As used herein, the phrase "hydrophile-lipophile balance (HLB) number" refers to a measure of the degree to which a surfactant is hydrophilic. This measurement is determined by methods such as those set forth in Griffin, W. C. "Classification of Surface-Active Agents by 'HLB,'" *J Cosmet Sci,* 1949, 1: 311; also Griffin, W. C. "Calculation of HLB Values of Non-Ionic Surfactants," *J Cosmet Sci,* 1954, 5: 259; and Davies, J. T. "A quantitative kinetic theory of emulsion type, I. Physical chemistry of the emulsifying agent," Gas/Liquid and Liquid/Liquid Interface. *Proceedings of the International Congress of Surface Activity,* 1957: 426-438.

As used herein the phrase "organic solvent" refers to a solvent compound that is composed of carbon atoms. Non-limiting examples of organic solvents include methanol, ethanol, propanol, phenol, acetone, dimethylformamide, butane, pentane, hexane, tetrahydrofuran, benzene, and acetic acid.

As used herein the term "antisolvent" refers to a solvent that does not substantially solubilize the solute, which is solubilized by the organic solvent. A non-limiting example of an antisolvent is water. Other examples include water that is buffered at an appropriate pH in order to suppress ionization of the solute and correspondingly minimize its solubility in the aqueous phase. Yet other examples include buffered aqueous solvents that have a pH which results in high saturation of a drug in the organic solvent.

As used herein, the phrase "buffered aqueous solution" refers to a water-based solution that is buffered. Buffered herein refers to a solution having the ions, acids, bases, conjugate acids, and conjugate bases such that the solution maintains an approximate pH despite the addition of small amounts of additional acids or bases.

As used herein, the phrase "flash nanoprecipitation" refers to a method of producing organic nanoparticles by mixing an organic solvent, an antisolvent, a molecule to include in the nanoparticle, and a pharmaceutically-acceptable polymer in a mixer that is capable of providing an energy dissipation rate of approximately $10^4$-$10^5$ W/kg of mixed solvents during the mixing process. Stable nanoparticles formed by flash nanoprecipitation can be isolated from the mixer after production.

As used herein, the phrases "co-freeze dry" or "co-freeze drying" refers to the process of freezing or cooling two substances simultaneously while also extracting moisture and/or water from the substances. For example, when a nanoparticle is co-freeze dried with a cryoprotectant, the nanoparticle and the cryoprotectant are simultaneously cooled and moisture is extracted or removed, e.g., by use of a vacuum system, from both.

As used herein, the term "cryoprotectant" refers to a substance, e.g., sugar or a beta-cyclodextrin, which serves to protect another substance, e.g., a nanoparticle formed by FNP, against the deleterious effects of freezing, e.g., degradation of the nanoparticle, change in size, change in shape.

As used herein, the phrase "minimum change in particle size" refers to the absence of a major change in the particle size. For example, when a dried nanoparticle is dispersed in water, the size of the nanoparticle minimally changed if the size of the dispersed nanoparticle is not greater or less than 40% of the size of the nanoparticle before it is dispersed in water.

As used herein, the phrase "minimum change in particle morphology" refers to the absence of a major change in the particle morphology. For example, if the nanoparticle is spherical, the morphology is considered minimally changed if the nanoparticle is semi-spherical, oval, or otherwise generally circular in three dimensions. The morphology of a spherical nanoparticle is not minimally changed if the nanoparticle degrades into its constituent components or develops faceted edges.

As used herein, the term "mixer" refers an apparatus useful for combining substances recited herein, such as, but not limited to, a multi-inlet vortex mixer or a confined impinging jet mixer.

The terms "formulation," "composition," and "preparation" as used herein are equivalent terms referring to a composition of matter suitable for pharmaceutical use (i.e., producing a therapeutic effect as well as possessing acceptable pharmacokinetic and toxicological properties).

An "effective amount" is an amount sufficient to contribute to the treatment, prevention, or reduction of a symptom or symptoms of a disease. Also an "effective amount" is an amount sufficient to achieve the desired result on the process or condition, and it accordingly will depend on the ingredient and the desired result. An "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, or reducing the likelihood of the onset (or reoccurrence) of a disease or its symptoms. The full prophylactic effect does not necessarily occur by administration of one dose, and may occur only after administration of a series of doses. Thus, a prophylactically effective amount may be administered in one or more administrations.

The term "therapeutically effective amount" as used herein also refers to that amount of the therapeutic agent sufficient to ameliorate one or more aspects of the disorder. For example, for the given aspect (e.g., length of incidence), a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The terms "treat", "treating," and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

The terms "subject," "patient," "individual," and the like as used herein are not intended to be limiting and can be generally interchanged. That is, an individual described as a "patient" does not necessarily have a given disease, but may be merely seeking medical advice. The "patient" or "subject in need thereof" may be prone to a condition that can be treated by administration of a pharmaceutical composition as provided herein. The term "subject" may also include all members of the animal kingdom prone to suffering from an indicated disorder. Non-limiting examples include humans, other mammals and other non-mammalian animals.

As used herein, the term "administration" refers to the process of managing or supervising the use of a substance. For example, the phrase "administering an effective amount of nanoparticles" refers to the process of managing or supervising the use of an amount of nanoparticles by another, e.g., a patent in need thereof.

As used herein, the term "polydispersity index" is a measure of the distribution of particle sizes for a collection of particles, e.g., nanoparticles.

As used herein, the term "span" refers to a measure of the spread or width of the distribution of particle sizes for a collection of particles, e.g., nanoparticles. Span is calculated as follows: $(d_{90}-d_{10})/d_{50}$; wherein $d_{90}$ is the particle size which is at or below 90% of the total distribution of particle sizes for a collection of particles; $d_{50}$ is the particle size which is at or below 50% of the total distribution of particle sizes for a collection of particles; and $d_{10}$ is the particle size which is at or below 10% of the total distribution of particle sizes for a collection of particles. As used in the definition of "span," the distribution of particles having particle sizes at or below $d_{90}$ is referred to as the cumulative undersize distribution at the 90%. Similarly, the distribution of particles having particle sizes at or below $d_{50}$ is referred to as the cumulative undersize distribution at the 50%, and the distribution of particles having particle sizes at or below $d_{10}$ is referred to as the cumulative undersize distribution at the 10%. In this definition, $d_{10}$, $d_{50}$, and $d_{90}$ are the sizes, below which the cumulative number of particles have particle sizes under 10, 50, and 90%, respectively, of the total distribution of particle sizes.

As used herein, the term "stability" refers to the tendency of a compound, specie, nanoparticle, or other potentially reactive entity to not react or degrade for a period of time. For example, the nanoparticles of the present invention are stable nanoparticles. In this regard, the nanoparticles are stable with respect to aggregation, degradation, or reactions which would effect the intended functionality of the nanoparticles for at least fifteen minutes after they are generated.

III. Nanoparticles

In some embodiments, the present invention provides a nanoparticle having a spherical particle morphology and an average particle diameter of about 50 nm to about 200 nm. The nanoparticle includes: a molecule having a Log P value of about 3 or above; an amphiphilic diblock copolymer or a surfactant; and a pharmaceutically-acceptable hydrophilic polymer. In some other embodiments, the pharmaceutically-acceptable hydrophilic polymer is polyvinyl pyrrolidone, polyvinyl alcohol, or hydroxypropyl methylcellulose. In certain embodiments, the hydrophilic polymer is a polymer with suspending properties. In other embodiments, the nanoparticle has an average particle diameter of about 75 to about 200 nm; about 100 to about 200 nm; about 125 to about 200 nm; about 150 to about 200 nm; about 175 to about 200 nm; In yet other embodiments, the nanoparticle has an average particle diameter of about 75 to about 175 nm; about 100 to about 150 nm; about 125 to about 150 nm; about 150 to about 175 nm; or about 75 to about 150 nm. In some embodiments, the molecule having a Log P value of about 3 or above is a hydrophobic molecule.

In some embodiments, the nanoparticle includes a molecule having a Log P value of about 3, 3.5, 4, 4.5, 5, 5.5, 6, or 6.5. In some other embodiments, the nanoparticle includes a molecule having a Log P value of about 3 to about 4; about 3 to about 5; about 3 to about 6, about 4 to about 5; about 4 to about 6; or about 5 to about 6.

In some embodiments, the nanoparticle formulation has an average particle diameter of about 70 nm. In some other embodiments, the nanoparticle formulation has an average particle diameter of 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 nm.

In some embodiments, the nanoparticle formulation includes a molecule that has a Log P value of about 3 or above and is present in an amount up to about 80% loading. In some other embodiments, the molecule has a Log P value of about 3 or above and is present in an amount up to about 78, 76, 74, 72, 7, 68, 66, 64, 62, 6, 58, 56, 54, 52, 40, 38, 36, 34, 32, 30, 28, 26, 24, 22, 20, 18, 16, 14, 12, 10, 8, 6, 4, or 2% loading.

In some other embodiments, the amphiphilic diblock copolymer includes polyethylene glycol and a hydrophobic biodegradable polymer; and the surfactant is lecithin, cholesterol, D-α-Tocopherol polyethylene glycol 1000 succinate or one with similar hydrophile-lipophile balance (HLB) number. In some embodiments, the amphiphilic diblock copolymer includes polyethylene oxide. In certain embodiments, a surfactant is suitable to stabilize the nanoparticle without the need for, or presence of, an amphiphilic diblock copolymer.

Amphiphilic diblock copolymers which are suitable for use with the present invention include, but are not limited to, poly(ethylene) glycol)-polylactic acid (PEG-PLA); poly (ethylene) glycol)-poly caprolactone (PEG-PCL); poly(ethylene) glycol) -polylactic-co-glycolic acid (PEG-PLGA); methoxypolyethylene glycol-polylactic acid (MePEG-PLA); methoxypolyethylene glycol-poly caprolactone (MePEG-PCL); methoxypolyethylene glycol-polylactic-co-glycolic acid (MePEG-PLGA); and polyethylene oxide-Polybutadiene (PEO-PBD).

Pharmaceutically acceptable hydrophilic polymers which are suitable for use with the present invention include, but are not limited to, polyvinyl pyrrolidone (PVP); polyvinyl alcohol (PVA); polyethylene glycols (PEG); and hydroxypropyl methylcellulose (HPMC); poloxamers (e.g., poloxamer P124, 188, 237, 338, 407).

Biodegradable polymers which are suitable for use with the present invention include, but are not limited to, polylactic-co-glycolic acid (PLGA); poly caprolactone (PCL); polylactic acid (PLA); poly(butyl)cyanoacrylate (PBCA); and chitosan.

Surfactants which are suitable for use with the present invention include, but are not limited to, cationic surfactants, e.g., benzalkonium chloride; benzethonium chloride; cetrimide. Surfactants which are suitable for use with the present invention include, but are not limited to, anionic surfactants, e.g. docusate sodium; sodium lauryl sulfate. Surfactants which are suitable for use with the present invention include, but are not limited to, non-ionic surfactants, e.g., glyceryl monooleate; sorbitan esters (e.g., sorbitan monolaurate, sorbitan monooleate, sorbitan monopalmitate, sorbitan sesquioleate, sorbitan trioleate); polyoxyethylene sorbitan fatty acid esters (e.g., polysorbates 20, 40, 60, 65, 80 and 85); polyoxyethylene alkyl ethers (e.g., polyethylene glycol monocetyl ether, polyethylene glycol monolauryl ether, polyethylene glycol monooleyl ether, polyethylene glycol monostearyl ether); and d-α-tocopheryl polyethylene glycol 1000 succinate (Vitamin E TPGS);

A. Pharmaceutically-acceptable Polymers

The present invention also provides pharmaceutical compositions of the nanoparticles described herein. Also, pharmaceutically-acceptable polymers suitable for use with the present invention include polyvinyl pyrrolidone (PVP) and polyvinyl alcohol (PVA). These pharmaceutically-acceptable polymers improve the stability of the nanoparticles formed by FNP by suppressing and, or, preventing particle growth and particle aggregation as a function of the concentration of the polymer.

The stabilizing effect of these pharmaceutically-acceptable polymers is illustrated in FIG. 1. The instability of nanoparticles, which include molecules having a relatively lower Log P, may be due to the relatively weak interaction between the hydrophobic part of the amphiphilic block copolymer and the molecule having a relatively lower Log P. Accordingly, the amphiphilic stabilizer will be more prone to dissociation from the co-precipitating compound, and hence will be less effective for maintaining the nanostructure integrity. In these nanoparticles, a pharmaceutically-acceptable polymer such as PVP or PVA may act as a protective colloid for the particles by forming an extensive hydrogen bonding network with the hydrophilic PEG block of the copolymer on the particle surface. By forming a protective colloid for the particles and by forming an extensive hydrogen bonding network, the pharmaceutically-acceptable polymers stabilize the nanoparticles from Ostwald ripening and/or aggregating with other nanoparticles.

B. Drugs Suitable for Use

In some embodiments, the molecule having a Log P value of about 3 or above is a drug, or a compound known to have therapeutic effects. In some other embodiments, the molecule having a Log P value of about 3 or above is a drug selected from itraconazole, Ibuprofen, or curcumin.

Drugs which are suitable for use with the present invention include, but are not limited to, curcumin, ibuprofen, flurbiprofen, itraconazole, phenytoin, indomethacin, doxorubicin, Huperzine A. Other drugs which are suitable for use with the present invention include, but are not limited to, drugs having limited aqueous solubility, e.g., drugs having an aqueous solubility of less than 0.5 mg/ml.

IV. Method of Making the Nanoparticles

In some embodiments, the present invention provides a method of making a nanoparticle. The method includes these steps: (1) mixing in a mixer an organic solvent, an antisolvent, a molecule having a Log P value of about 3 or above, and a pharmaceutically-acceptable hydrophilic polymer with suspending properties such as polyvinyl pyrrolidone, polyvinyl alcohol or hydroxypropyl methylcellulose; and (2) producing spherical nanoparticles having an average particle diameter of about 50 nm to about 200 nm by flash nanoprecipitation. In some embodiments, the method further includes isolating the nanoparticles from the mixer.

In some embodiments, the organic solvent includes an amphiphilic diblock copolymer or a surfactant. In other embodiments, the organic solvent includes an amphiphilic diblock copolymer. In yet other embodiments, the organic solvent includes a surfactant. In some other embodiments, the organic solvent includes an amphiphilic diblock copolymer and a surfactant. In other embodiments, the antisolvent is water. In yet other embodiments, the antisolvent is a buffered aqueous solution. In some embodiments, the buffered aqueous solution is buffered to maintain an approximate pH of 0, 1, 2, 3, 4, 5, 6, 7, 7, 8, 9, 10, 11, 12, 13, or 14.

In some other embodiments, the mixer is selected from the group consisting of a confined impinging jet mixer and a multi-inlet vortex mixer.

The present invention provides methods of making the nanoparticles described herein. In some embodiments, a mixer suitable for use with the present invention includes a multi-inlet vortex or a confined impinging jet mixer. In yet other embodiments, the mixer is one capable of providing an energy dissipation rate of approximately $10^4$-$10^5$ W/kg of mixed solvents during the mixing process. Mixers that are suitable for use with the present invention and can provide an energy dissipation rate of approximately $10^4$-$10^5$ W/kg during the mixing process prevent the nanoparticles generated in situ from aggregating as a consequence of each nanoparticle's high surface-energy. Without a sufficient energy dissipation rate during the mixing process, nanoparticles might aggregate in order to reduce each nanoparticle's high surface-energy. In some embodiments, the mixer suitable for use with the present invention includes a reaction vessel or container having a specific surface to volume ratio. In some other embodiments, the mixer includes inlet and outlet ports which have a specific aperture diameter. In some embodiments, the mixer's internal surface to volume ratio is an optimized value based on the viscosity of the solutions used to form the nanoparticles. In yet other embodiments, the mixer's inlet and outlet ports have aperture diameters which are optimized based on the viscosity of the solutions used to form the nanoparticles.

Cryoprotectants which are suitable for use with the present invention include, but are not limited to, glucose; sucrose; trehalose; lactose; sodium glutamate; polyvinly pyrrolidone; cyclodextrins (e.g. hydroxypropy-β-cyclodextrin); glycerol; maltose; mannitol; and saccharose.

In any of the methods described herein, the drug may be present in a water-soluble salt form. In any of the methods described herein, the molecule having a Log P value of about 3 or above may be present in a water-soluble salt form.

In any of the methods described herein, the method optionally further include a neutralization step. In certain embodiments, the neutralization step involves the use of a base or an acid in the aqueous phase during the precipitation process. In some embodiments, the neutralization step involves the use of an acid. In other embodiments, the neutralization step involves the use of a base.

In some embodiments, the present invention provides a method of making a nanoparticle. The method includes these steps: (1) mixing in a mixer an organic solvent, an antisolvent, a molecule having a Log P value of about 3 or above that is in a water-soluble salt form, and a pharmaceutically-acceptable hydrophilic polymer with suspending properties such as polyvinyl pyrrolidone, polyvinyl alcohol or hydroxypropyl methylcellulose; and (2) producing spherical nanoparticles having an average particle diameter of about 50 nm to about 200 nm by flash nanoprecipitation. In some embodiments, the method further includes isolating the nanoparticles from the mixer. In some embodiments, the method further includes a neutralization step. In certain embodiments, the neutralization step involves the use of a base or an acid in the aqueous phase during the precipitation process. In some embodiments, the neutralization step involves the use of an acid. In other embodiments, the neutralization step involves the use of a base.

V. Method of Drying the Nanoparticles

In some other embodiments, the present invention provides a method of drying a nanoparticle, as set forth herein, to yield a solid powder, including co-freeze drying the nanoparticle with a cryoprotectant, such as a sugar or a beta-cyclodextrin, at a concentration of not more than 2% w/v. In certain embodiments, the concentration of the cryoprotectant is not more than 1.5%; 1.0%; or 0.5%. In some embodiments, the solid powder is readily dissolved in water. In some other embodiments, the solid powder completely dissolves in water. In yet other embodiments, the solid powder quickly dissolves in water without leaving a precipitate. In some other embodiments, the solid powder is readily dissolved in water without substantially changing the particle size or particle morphology. In some embodiments, the solid powder is dissolved in water and the particle size does not change more than 5, 10, 15, 20, 25, 30, 35, 40, 45, or 50%. In certain embodiments, after being dissolved in water, the nanoparticles of the present invention do not change their particle diameter by more than 1, 2, 5, 10, 12, 15, 18, 20, 25, or 30 nm.

VI. Pharmaceutical Compositions

In some embodiments, the present invention provides a method of delivering a molecule having a Log P value of about 3 or above, which is a part of the nanoparticle described in this application. The method includes the step of administering an effective amount of such a nanoparticles to an intended recipient. In some other embodiments, the molecule having a Log P value of about 3 or above is a drug. In some embodiments, the drug is itraconazole, Ibuprofen, or curcumin.

The present invention also provides pharmaceutical compositions of the nanoparticles described herein.

A. Administration

The nanoparticles of the present invention are useful in the manufacture of a pharmaceutical composition or a medicament. A pharmaceutical composition or medicament can be administered to a subject in need thereof.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

B. Routes of Administration

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated. In particular, the technique set forth in Example 1 is useful for formulating drug-containing nanoparticles for oral or parenteral delivery.

Suitable formulations for transdermal application include an effective amount of a nanoparticle formulation of the present invention optionally with a carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. The present invention provides tablets and gelatin capsules comprising the nanoparticles of the present invention or a dried solid powder of the nanoparticles of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Nanoparticles of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the nanoparticles of the present invention may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The nanoparticles can also be formulated in rectal compositions, for example, suppositories or retention enemas, for example, containing conventional suppository bases, for example, cocoa butter or other glycerides.

Furthermore, the nanoparticles can be formulated as a depot preparation. Such long-acting formulations can be administered by implantation (for example, subcutaneously or intramuscularly) or by intramuscular injection. Thus, for example, the nanoparticles can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a nanoparticle formulation as described herein, and (ii) optionally another therapeutic agent. When used with a compound of the present invention, such nanoparticles may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

C. Dosage

Pharmaceutical compositions or medicaments can be administered to a subject at a therapeutically effective dose to prevent, treat, or control a target disease or condition as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular formulation in a particular subject. A unit dosage for oral administration to a mammal of about 50 to 70 kg may contain between about 5 and 500 mg of the active ingredient. A unit dosage for a particularly potent drug may be lower than for other less potent drugs. Additional unit dosages which are suitable for use with the present invention include dosages in the amount of 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mg. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

EXAMPLES

Example 1

Role of Cholesterol in the Nanoprecipitation of Itraconazole with Amphiphilic Stabilizers The purpose of this study was to investigate the roles of cholesterol (CLT) in the formulation of itraconazole (ITC) nanoparticles with selected amphiphilic stabilizers (ASs).

In this study, ITC nanoparticles were produced using a four-stream multi-inlet vortex mixer (MIVM). One stream of the mixer contained an organic solvent (dimethylformamide, DMF) while the other three streams consisted of deionized water serving as an antisolvent. In one experiment, the organic solvent was dimethylformamide (DMF). ITC, at a concentration of 5 mg/ml, CLT, at a concentration of 1-5 mg/ml, and ASs, at a concentration of 2.5-5 mg/ml, were dissolved in DMF. Rapid mixing of the organic and aqueous phases in the mixer was controlled with two digital programmable syringe pumps operating at a defined flowrate. The organic stream in inlet A and one of the aqueous streams in inlet C were set at the same flowrate. The remaining two aqueous streams, in inlets B and D, respectively, formed another flow equivalent pair. The flowrate of inlets B and D was set at 9 times higher than that of inlets A and C in order to induce a sufficiently high supersaturation level of ITC for rapid precipitation. The effects on the particle size and stability of the resulting nanoparticles as a function of CLT and the selected ASs were assayed by dynamic light scattering particle sizing and visual examination. In one experiment the selected ASs was polyethylene glycol-polylactic acid PEG-PLA, having a molecular weight of approximately 5,000-10,000 g/mol, and d-α-tocopheryl polyethylene glycol 1000 succinate (TPGS).

This study demonstrated that, in the presence of PEG-PLA or TPGS, ITC nanosuspensions with mean particle sizes below 200 nm and polydispersity indices less than 0.3 could be readily and reproducibly generated. Aggregation and particle size growth occurred within hours after particle formation. The addition of CLT improves the stability and results in the mean ITC particle size being substantially reduced to less than 100 nm. CLT appeared to be a factor influencing the stability of the ITC nanosuspensions by ASs through an enhancement of interaction between ITC and ASs.

Based on this study, it was demonstrated that CLT is an effective co-stabilizer for the nanoparticle formulations of ITC and also for other drugs of similar physicochemical nature which cannot be stabilized by amphiphilic excipients alone.

Example 2

Influence of Process Variables on the Nanoprecipitation of Ibuprofen Using a Multi-inlet Vortex Mixer The purpose of this study was to investigate the effect on the formulation of ibuprofen-containing nanoparticles as a function of the process variables used in flash nanoprecipitation in a four-stream multi-inlet vortex mixer (MIVM).

In this study, Ibuprofen (IBP) and an amphiphilic diblock co-polymer (ADCP) stabilizer composed of polyethylene glycol (PEG) and polylactic acid (PLA) were dissolved in a water-miscible organic solvent. The organic solution was then injected along with three other streams of deionized water into an MIVM through its four inlets by means of two syringe pumps. Vigorous mixing, in the mixer, of the organic phase and the deionized water resulted in an extremely high supersaturation level within milliseconds and also rapid precipitation of ADCP-protected IBP nanoparticles. The effects on the particle size and size distribution of the resulting suspensions as a function of drug concentration, molecular weight of ADCP, drug to ADCP ratio, type of organic solvent, organic solvent to water volume ratio, and Reynolds number (Re) during mixing were assessed using a dynamic light scattering (DLS) particle size analyzer. The different types of organic solvents assessed included acetone, tetrahydrofuran, and dimethylformamide. Drug loading efficiencies of different formulations were determined by high performance liquid chromatography.

This study demonstrated that the mean particle sizes and polydispersity indices of the suspensions were respectively within the ranges of 30-90 nm and 0.03-0.24 when acetone is used as the organic solvent. Using multivariate analysis, this study also demonstrated that the dominant factor which determines particle size was the molecular weight of the ADCP. The next most dominant factor which determines particle size was drug concentration. Furthermore, the next most dominant factor which determines particle size was Re. In addition, the next most dominant factor which determines particle size was the acetone to water ratio. Lastly, the next most dominant factor which determines particle size was determined to be the drug to ADCP concentration ratio. Nanoparticle suspensions prepared with acetone and dimethylformamide as the organic phase had nanoparticles with approximately equal sizes in comparison. However, those nanoparticles obtained using tetrahydrofuran displayed significantly larger average particle size (p=0.002). The drug loading efficiency of the nanoparticles was approximately 75% (w/w).

Based on this study, it was demonstrated that polymer-stabilized IBP nanoparticles with high drug loading can be reproducibly formulated via flash nanoprecipitation using a four-stream MIVM. The molecular weight of ADCP and drug concentration appeared to be the primary factors which determined the resulting particle size of the nanoparticle formulations.

Example 3

Flash Nanoprecipitation of Ibuprofen from Solutions Using a Confined Impinging Jet Mixer The purpose of this study was to formulate stable and uniform ibuprofen-containing nanoparticles via flash nanoprecipitation using a confined impinging jet (CIJ) mixer.

In this study, Ibuprofen and an amphiphilic diblock co-polymer (ADCP) stabilizer, which was composed of polyethylene glycol (PEG) and polylactic acid (PLA) were dissolved in acetone. In some experiments, the molecular weights of the PEG-PLA was approximately 2000 g/mol; or 2000-8000 g/mol; or 2000-10,000 g/mol; or 5000-10000 g/mol. Hydrophilic polymer stabilizers were dissolved in water. In some experiments, the hydrophilic polymer stabilizers were polyvinyl alcohol, having a molecular weight of approximately 50,000 g/mol or hydroxypropyl methylcellulose, having a molecular weight of approximately 26,000 g/mol. Equal volumes of 2.5 mL of both solutions were injected into a confined impinging jet (CIJ) mixer simultaneously at the same flow rate using a syringe pump. Vigorous mixing of the organic and antisolvent aqueous phases in the mixer resulted in an extremely high supersaturation level within milliseconds and also rapid precipitation of ADCP-protected ibuprofen nanoparticles. The resulting nanosuspension was diluted with 45 mL water upon exit from the mixer. The effects on the particle size distribution of the suspension as a function of ADCPs and hydrophilic polymers were assessed using a dynamic light scattering (DLS) particle sizer. Drug yield and drug entrapment efficiency of different formulations were determined by high performance liquid chromatography.

This study demonstrated that Ibuprofen nanoparticles prepared with ADCP stabilizers alone exhibited mean particle sizes and polydispersity indices in the ranges of 50-120 nm and 0.04-0.26 nm respectively. Addition of hydrophilic polymers to the aqueous phase resulted in an increase in the size of the particles. Precipitation with ADCPs of higher molecular weights also afforded larger particles. The mass ratio of ADCP to ibuprofen in the suspending medium was important with regard to the stability of the suspension. A minimum ADCP:drug mass ratio of 1:1 is required in order to maintain the dispersion of the particles effectively. Drug yield and drug entrapment efficiency for all formulations were approximately 35% and 75% respectively when the mass ratio was 1:1. This corresponds to a 50% theoretical drug yield for total precipitation.

Based on this study, polymer-stabilized ibuprofen nanoparticles with high drug yield can be reproducibly prepared via flash nanoprecipitation using the CIJ mixer. Furthermore, these nanoparticles have an average particle diameter which was approximately below 100 nm.

Example 4

Comparative Assessment of the Performance between Confined Impinging Jet and Multi-inlet Vortex Mixers for Controlled Production of Curcumin Nanoparticles The purpose of this study was, in part, to evaluate and to compare the controlled production of curcumin (CUR) nanoparticles in a confined impinging jet (CIJ) mixer with the same in a multi-inlet vortex mixer (MIVM).

In the two-stream CIJ mixer, CUR nanoparticles were generated by intensely mixing equal volumes of an organic stream with an aqueous stream as the antisolvent. The organic solution contained CUR, at a concentration of 10 mg/ml, and an amphiphilic block copolymer stabilizer, at a concentration of 10 mg/ml. In certain experiments, the amphiphilic block copolymer stabilizer was polyethylene glycol-polylactic acid (PEG-PLA), which has a molecular weight of approximately 2,000-10,000 g/mol. The mixture was subsequently diluted with approximately 45 ml water upon exit from the mixer. For the four-stream MIVM, similar experimental conditions were employed. For example, the four-stream MIVM was used with an organic stream containing CUR and the aforementioned PEG-PLA stabilizer. The other three streams were composed of water only. In both mixers, the stream flow rates were controlled by means of a digital progammable syringe pumps.

While not varying stream flowrates and concentrations of CUR and PEG-PLA, the effect on the produced nanoparticle's particle size and stability was assessed by dynamic light scattering particle size analysis and visual examination as a function of the type of organic solvent used. Three different organic solvents were evaluated by this method. These organic solvents included acetone (ACT), dimethylformamide (DMF), and tetrahydrofuran (THF).

The results of this study demonstrated that, irrespective of the organic solvents used, both mixers attained homogenous mixing at Reynolds number (Re) larger than 3000. This homogenous mixing at Re larger than 3000 is indicative that the dominant mixing mechanism changed from turbulence-controlled to diffusion-controlled. In addition, the particle size—Re profiles were approximately equal for the two mixers evaluated. However, turbulent fluctuations were observed in the systems employing DMF and THF at Re above 4000 whereas turbulent fluctuations were not observed in the systems employing ACT. Furthermore, the ACT system resulted in the smallest particle sizes. This may be explained by the greater diffusivity of ACT in the aqueous medium which enabled more efficient molecular mixing. The CIJ mixer also yielded nanoparticles with a narrower particle size distribution as compared to the MIVM. Both mixers yielded nanoparticles that had comparable stabilities as evidenced by the particle growth and aggregation about two hours after preparation.

Based on this study, it was demonstrated that both mixers were capable of yielding CUR nanoparticles of comparable mean size and stability. However, the CIJ mixer, as compared to the MIVM mixer, yielded nanoparticles with a narrower particle size distribution.

Example 5

Controlled Production of Polymer-stabilized Drug Nanoparticles via Flash Nanoprecipitation The purpose of this study was, in part, to assess the effect on drug nanoparticle production as a function of the processing parameters use in flash nanoprecipitation.

In this study, three drugs were incorporated into a nanoparticle formulation by flash nanoprecipitation in a confined impinging jet (CIJ) mixer by mixing a solution of the drug and an amphiphilic co-block polymer stabilizer with an equal volume of water (2.5 mL) as an antisolvent. In one experiment, the amphiphilic co-block polymer stabilized was polyethylene glycol-polylactic acid (PEG-PLA), which has a molecular weight of approximately 2,000-10,000 g/mol, in acetone (10 mg/mL). Pharmaceutically approved polymer stabilizers were also added to the aqueous phase (0.5 mg/mL) in some experiments. In some experiments, the pharmaceutically approved stabilizer was polyvinyl pyrrolidone, which has a molecular weight of approximately 50,000 g/mol or polyvinyl alcohol, which has a molecular weight of approximately 50,000 g/mol. The organic and aqueous phases were intensely mixed by introducing the two solution comprising the organic and aqueous phases concurrently into the mixer at a specific flowrate using a syringe pump. The mixture was rapidly diluted with 45 mL of water upon exit from mixer.

The effect on nanoparticle particle size, polydispersity index, and zeta potential as a function of the solution flowrate, stabilizer system and drug-to-stabilizer mass ratio on the resulting nanoparticle suspensions was assessed using a dynamic light scattering (DLS) particle size analyzer.

The results of this study demonstrated that most freshly prepared nanoparticles were below 250 nm. Also, most of the nanosuspensions showed a slight increase in particle size with storage time, possibly due to particle aggregation or Ostwald ripening. An increase in solution flow rate resulted in smaller particles with a narrower size distribution. The narrower size distribution is indicative of rapid homogeneous nucleation under the influence of an extremely efficient mixing process. A decrease of the drug-to-stabilizer mass ratio, or the addition of hydrophilic polymer stabilizers to the aqueous stream, resulted in smaller and more stable particles. These smaller and more stable particles are likely due to the polymers' ability to prevent particle growth and aggregation. No significant correlation was observed between the zeta potential and shelf-life of the suspensions. The lack of correlation suggests that stabilization by charge repulsion plays a relatively insignificant role in these systems.

Based on this study, it has been shown that polymer-stabilized nanoparticles with an average particle diameter below 250 nm can be reproducibly generated by the CIJ mixer. Moreover, the effect on drug nanoparticle production as a function of solution flowrate, the type of stabilizer system, and the drug-to-stabilizer ratio has been assessed. These processing parameters are important parameters to consider in order to control the particle size and stability of the suspensions.

Example 6

Comparison with Certain Commercial Technologies

The purpose of this study was to compare particle size and particle size distribution metrics as a function of the method of forming the nanoparticles. In this study, the nanoparticles formed by FNP were compared with the nanoparticles formed by 1) milling/high pressure homogenization; 2) emulsification-solvent evaporation; and 3) supercritical fluid processing. Table 1 shows the results of this comparison.

Methods for engineering pharmaceutical nanoparticles can be broadly divided into two categories, namely, top-down and bottom-up approaches. The top-down approach encompasses various milling/high pressure homogenization methods and relies on the use of large amounts of energy in order to mill, crush, or break down the coarse particles down to the submicron or nanometer size range. In contrast, the methods of the present invention belong to the bottom-up approach and rely on the use of high supersaturation conditions in a solution in order to induce nanoparticle precipitation, rapidly. Top-down methods such as milling/high pressure homogenization are known to produce nanoparticles having a wide particle size distribution, highly energetic and charged surfaces, and which, as a consequence of having highly energetic and charged surfaces, tend to adhere and cohere with other nanoparticles. In contrast, the bottom-up methods of the present invention produce nanoparticles with a narrow size distribution and with advantageous surface properties. Compared with bottom-up methods, the methods of the present invention are less time-consuming, less costly and more amenable to scale-up.

TABLE 1

Comparison of methods of making nanoparticles.

| Category/Technology available | Milling/High pressure homogenization | Emulsification-solvent evaporation | Supercritical fluid processing | FNP |
|---|---|---|---|---|
| Mean particle size (nm) | 300-1000 | 80-250 | 100-500 | 50-200 |
| Particle size distribution | wide | moderately wide | moderately wide | narrow (span |

TABLE 1-continued

Comparison of methods of making nanoparticles.

| Category/<br>Technology<br>available | Milling/High<br>pressure<br>homogenization | Emulsification-<br>solvent<br>evaporation | Supercritical<br>fluid<br>processing | FNP |
|---|---|---|---|---|
| Processing<br>time | hours | hours | hours | often <1)<br>milli-<br>seconds |
| Drug loading | low,<br>generally<br><20% | low,<br>generally<br><20% | moderate,<br>generally<br><30% | high, up<br>to 80% |
| Processing<br>steps | 1 (but 20-50<br>cycles normally<br>required) | 2 | 1 | 1 |
| Control of<br>surface<br>properties | no | yes | yes | yes |
| Costs of<br>equipment and<br>Operation (e.g.<br>energy input) | high | medium | high | low |
| Operating<br>conditions | Normally<br>requires<br>elevated<br>temperature and<br>pressure | ambient<br>conditions<br>(vacuum may<br>be required<br>for drying) | Normally<br>requires high<br>pressure or<br>high<br>temperature | ambient<br>condi-<br>tions |
| Production<br>mode | batch | batch | batch/<br>continuous | conti-<br>nuous |
| Potential for<br>scaling-up | good | difficult | difficult | good |

Table 1 demonstrates that nanoparticles with smaller particle sizes and having a higher drug loading can be continuously produced by FNP rapidly and in a single—step. Additionally, the methods of the present invention are not limited by operating temperatures or pressures. As such, FNP was shown to be cost-effective and energy-saving as compared to methods such as milling/high pressure homogenization; emulsification-solvent evaporation; and supercritical fluid processing.

Example 7

Production of Stable Nanosuspensions Using FNP

Figure 2:
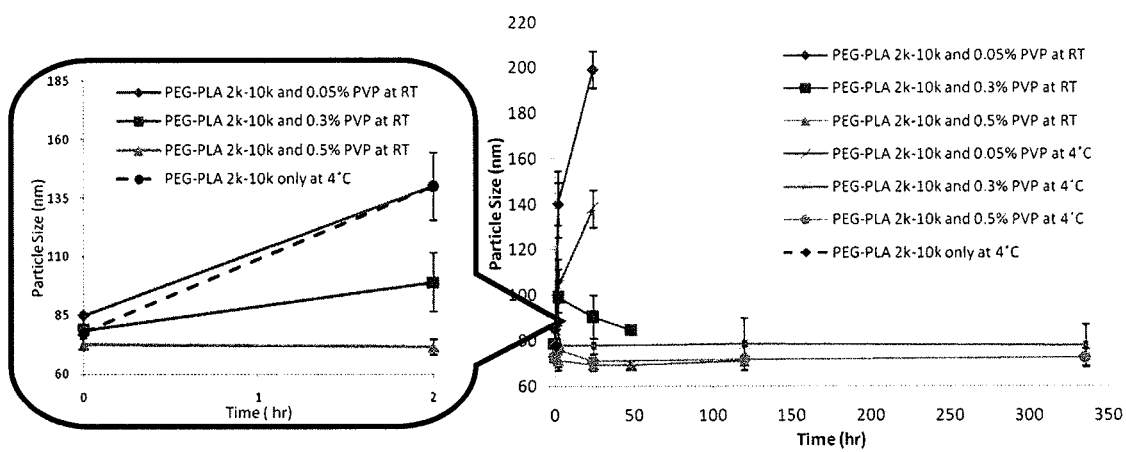
FIG. 2 shows the effect of storage time on particle size for samples containing PVP. The data points with particle size >200 nm, or visible precipitation, are classified as unstable formulations and omitted from the figure.
Figure 3:
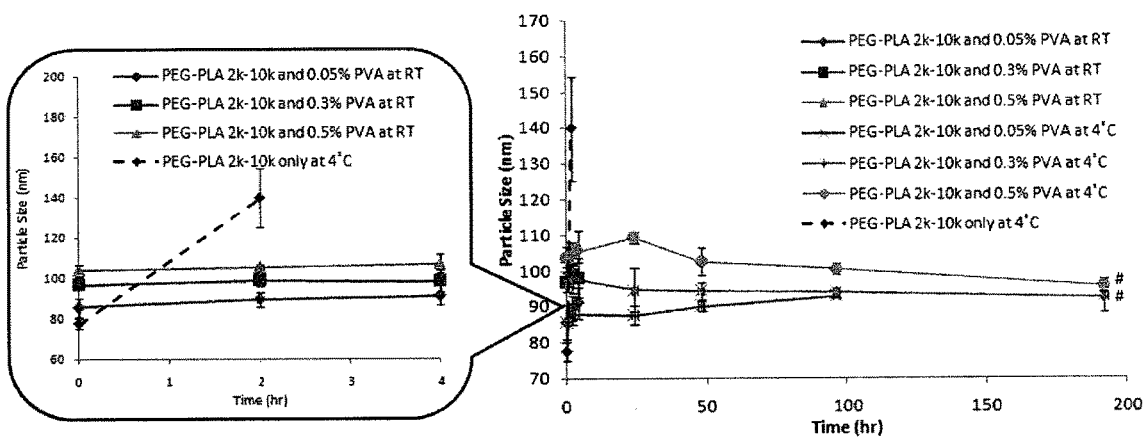
FIG. 3 shows the effect of storage time on particle size for samples containing PVA. The data points with particle size >200 nm, or visible precipitation, are classified as an unstable formulations and are omitted from the figure. (# indicates that 1 out of 3 samples are unstable formulations.
Figure 4:
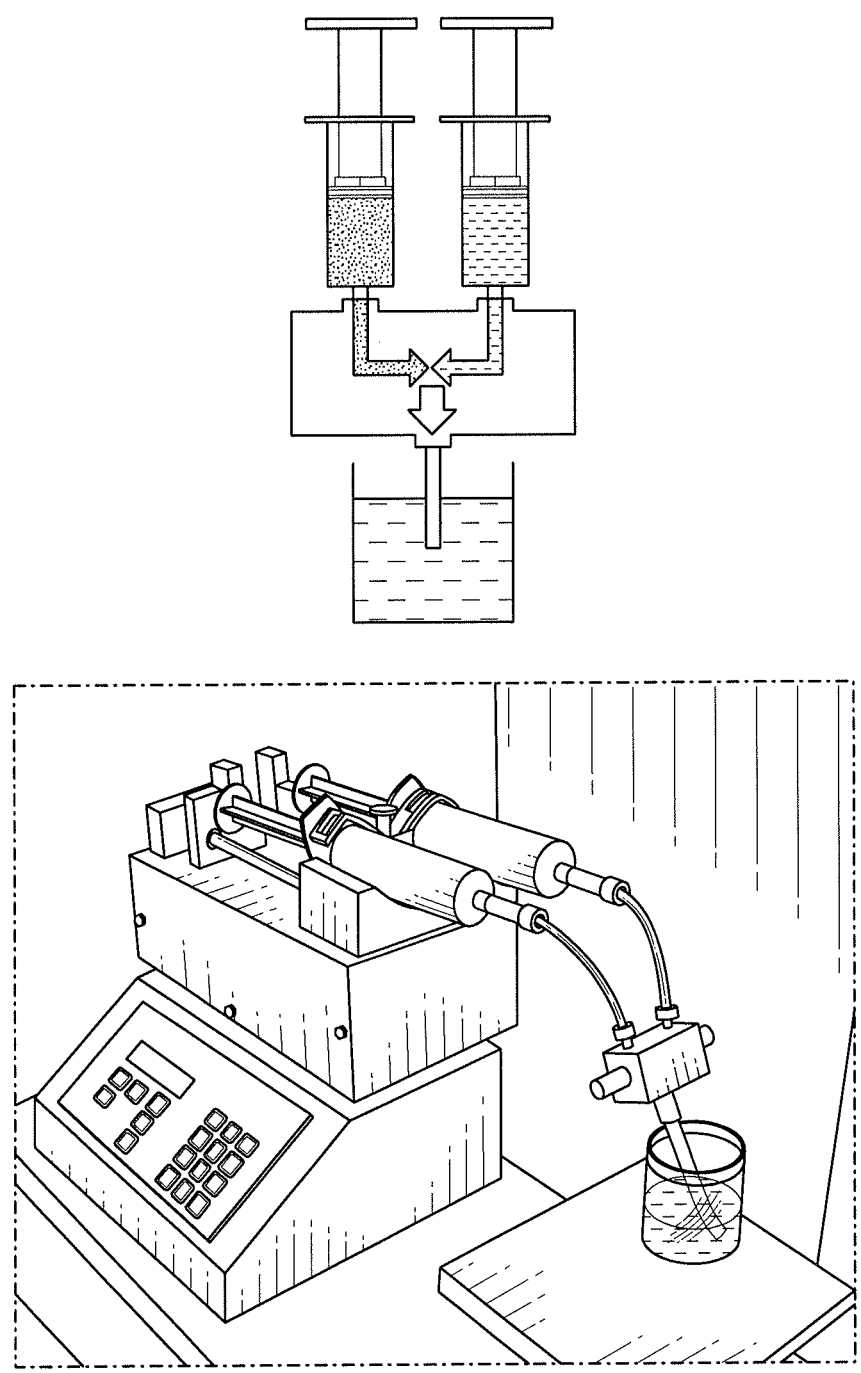
FIG. 4 shows the experimental setup of a confined impinging jet (CIJ) mixer (left) and typical experimental conditions for flash nanoprecipitation.
Figure 5:
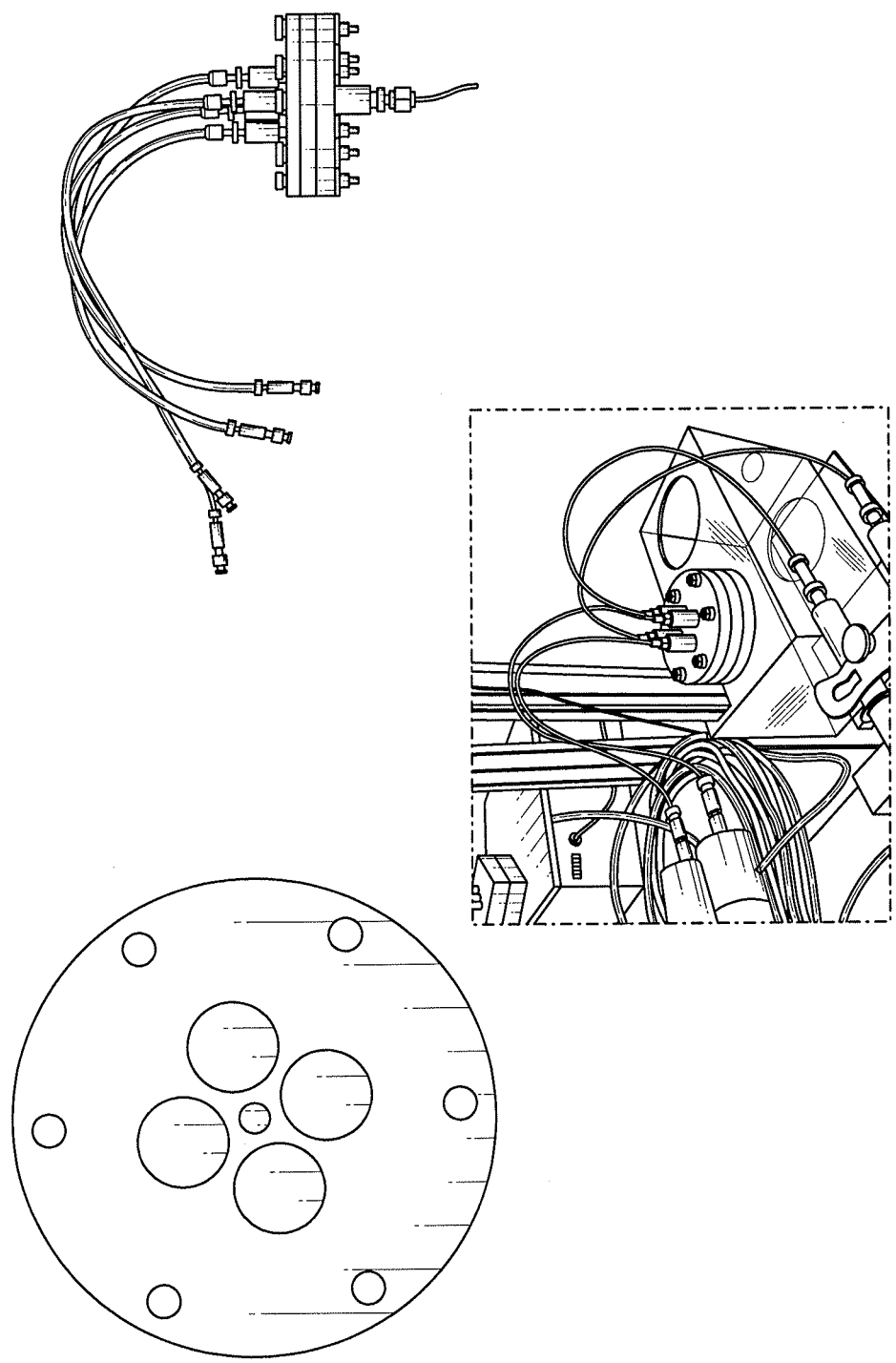
FIG. 5 shows a multi-inlet vortex mixer (left) and its internal design (right).
Figure 6:
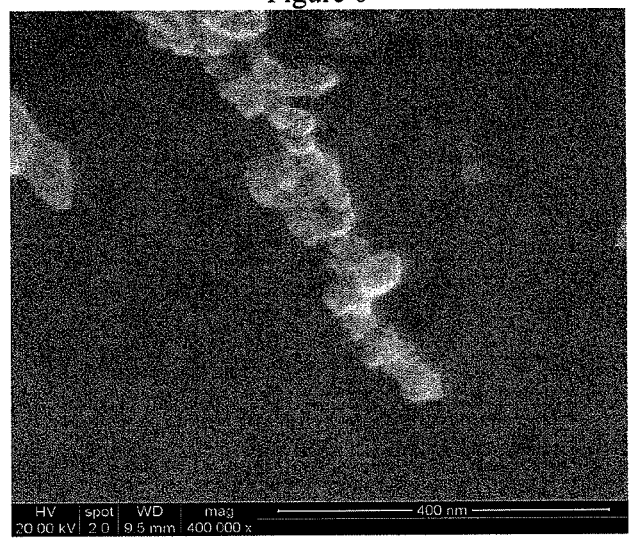
FIG. 6 shows a scanning electron micrograph of dried curcumin-containing nanoparticles at a magnification of 400,000×.

In this study, FNP was used to produce stable nanosuspensions of nanoparticles, having a mean particle size of about 70 nm and which contain the compound curcumin, which has a Log P=3. In order to minimize potential Ostwald ripening and aggregation of the nanoparticles, hydrophilic polymer stabilizers were incorporated into the nanosuspensions. As shown in FIG. 2, PVP, at a concentration of 0.5% w/v, effectively prolonged the shelf-life of the curcumin nanosuspension from a few minutes to five days at 20° C. and from a couple of hours to one month at 4° C. As shown in FIG. 3, PVA also afforded similar stability improvement on the formulation, but the effect was much less pronounced under ambient conditions. The stability-enhancing effects of both PVP and PVA were shown to be concentration dependent and more apparent at higher concentrations. It is thought that the adsorption of PVP or PVA onto the nanoparticles via extensive hydrogen bonding with the hydrophilic PEG block of the copolymer is a reversible process. As such, higher concentration of PVP or PVA are more effective at suppressing and, or, retarding their desorption which maintains the particle integrity. As shown in FIG. 6, the nanosuspensions which were produced by FNP were co-freeze dried with a cryogenic protectant after elimination of the organic phase, at a concentration of ~5% v/v, in the suspending medium by dialysis. In a similar study, the suspensions were co-spray dried with a suitable protective excipient. In addition, and as shown in FIG. 6, the dried particles were shown to be capable of being readily redispersed back into water with the mean particle size being increased by not more than 20 nm from the original value.

In this study it was also demonstrated that a number of pharmaceutically approved surfactants, e.g., lecithin, can be used in place of, or as a substitute for, the diblock copolymers. These surfactants were shown to be able to stabilize the nanoparticles of the present invention within a size range of 50-150 nm for certain drugs.

Example 8

Flash Nanoprecipitation of Doxorubicin Using a Multi-inlet Vortex Mixer

In this study, flash nanoprecipitation of DOX was used to produce polymer-stabilized doxorubicin (DOX) nanoparticle formulations in a four-stream multi-inlet vortex mixer (MIVM) by mixing organic solutions of doxorubicin hydrochloride, having a pKa of 8.4, and an amphiphilic diblock copolymer, e.g., polyethylene glycol-polylactic acid (PEG-PLA) and having a molecular weight of approximately 2000-1000 g/mol, in dimethylformamide (DMF). The drug:polymer ratio was varied in aqueous alkaline solutions containing sodium hydroxide (NaOH) or triethylamine (TEA). The solutions were prepared at different concentrations and pH conditions for converting the salt to the free base through neutralization. The resulting nanosuspensions were characterized with regard to the mean particle size and the size distribution by dynamic light scattering particle size analysis. For drug encapsulation efficiency, a UV-visible spectroscopy was used at 480 nm after removal of organic solvent and free drug by dialysis against deionized water.

This Example demonstrates that polymer-stabilized DOX nanoparticles having a mean particle size below 100 nm were obtained. Prolonged exposure of the formulation to alkaline conditions having a pH greater than 12 resulted in chemical degradation and particle growth of the polymer-stabilized DOX nanoparticles. When the pH was approximately 9-10, NaOH was a preferable neutralization medium as compared to TEA since higher DOX encapsulation efficiency was achieved and also because of the improved particle stability which resulted.

This Example also demonstrates a rapid, convenient, reproducible method for generating polymer-stabilized doxorubicin nanoparticles having a controllable particle size range through acid-base neutralization and antisolvent precipitation in a multi-inlet vortex mixer. The method of this Example was demonstrated to be suitable for use with other hydrophobic drugs which are present in a similar water-soluble salt form.

Example 9

Fabrication of Flurbiprofen Polymeric Nanoparticles by Flash Nanoprecipitation

The purpose of this study was to develop a flurbiprofen (FLU) nanoparticle formulation using flash nanoprecipitation.

In this study, a four-stream multi-inlet vortex mixer (MIVM) was employed with the aid of two syringe pumps to achieve efficient mixing of an organic phase containing FLU and an amphiphilic diblock copolymer as stabilizer with an aqueous phase containing a hydrophilic stabilizer.

The mixing created a sufficiently high supersaturation level for rapid precipitation of FLU nanoparticles. Particle size and stability was analyzed by dynamic light scattering (DLS) particle sizing and zeta potential measurement as a function of stream flowrate, organic-to-water volume ratio, the molecular weights of certain diblock copolymers used (e.g., polyethylene glycol-polylactic acid (PEG-b-PLA) having a molecular weight of approximately 2,000-5,000, 2,000-8,000, 2,000-10,000, 5,000-5,000, 5,000-8,000) and the presence of additional stabilizers [e.g., d-α-tocopherol polyethylene glycol 1000 succinate (TGPS)]. Certain nanosuspension formulations were subjected to dialysis to remove the organic solvent and free drug prior to freeze-drying with a cyoprotectant, e.g. 1% w/v hydroxypropyl âcyclodextrin (HP-â-CD)]. The dried samples were characterized with regard to particle size and particle morphology by scanning electron microscopy (SEM) and transmission electron microscopy (TEM). The dried samples were also characterized with regard to their ability to be disperse in water by dynamic light scatting size analysis.

The results of this study demonstrated that FLU polymeric nanoparticles with a mean size below 100 nm, a monomodal particle size distribution and roughly spherical morphology were readily and reproducibly generated. The use of a higher stream flowrate, a lower organic-water volume ratio and copolymer stabilizer with a larger PLA block (i.e. PEG-b-PLA, 2 k-10 k) yielded particles with smaller sizes and having an improved stability. The storage stability could be further improved, from about 1 day to more than 1 week, by the addition of TPGS at a concentration of about 0.125% w/v. The freeze-dried samples were able to be dispersed in water with limited change in particle size. In some experiments, the particle size change was within plus or minus 5 nm of the particles size in the original nanosuspension. The drug entrapment efficiency determined from the freeze-dried sample after redispersion in water was 20-25%.

This study demonstrated that FLU polymeric nanoparticles having a particle size below 100 nm were consistently produced using the four-stream MIVM. The production of these nanoparticles was analyzed as a function of the stream mixing rate, the organic-water volume ratio and the presence of additional co-stabilizers.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A collection of solid nanoparticles having a polydispersity index less than 0.3, wherein: the nanoparticles have a roughly spherical particle morphology and an average particle diameter of about 50 nm to about 200 nm;

each nanoparticle comprises: a core of a drug molecule having a Log P value of about 3 or above, an intermediate layer of an amphiphilic diblock copolymer, and an outer layer of a pharmaceutically-acceptable hydrophilic polymer;

wherein the drug molecule is present in the nanoparticles in an amount of greater than 50% w/w; and the nanoparticles are on average characterized by a change of particle size of not more than 40% after a storage time of at least 2 hours, wherein the solid nanoparticles are flash precipitated by a method comprising: mixing in a mixer an organic solvent, an antisolvent, a molecule having a Log P value of about 3 or above, and a pharmaceutically-acceptable hydrophilic polymer, wherein the mixer has an energy dissipation rate of approximately $10^4$-$10^5$ W/kg of mixed solvents during the mixing process, thereby producing a collection of roughly spherical nanoparticles.

2. The collection of solid nanoparticles of claim 1, wherein the pharmaceutically-acceptable hydrophilic polymer is polyvinyl pyrrolidone, polyvinyl alcohol, or hydroxypropyl methylcellulose.

3. The collection of solid nanoparticles of claim 1, having an average particle diameter of about 70 nm.

4. The collection of solid nanoparticles of claim 1, wherein the drug molecule is present in an amount up to about 80% w/w.

5. The collection of solid nanoparticles of claim 1, wherein the amphiphilic diblock copolymer comprises polyethylene glycol and a hydrophobic biodegradable polymer.

6. A method of making and drying the collection of solid nanoparticles of claim 1 to yield a solid powder, wherein said making comprises:

mixing in a mixer an organic solvent, an antisolvent, a molecule having a Log P value of about 3 or above, and a pharmaceutically-acceptable hydrophilic polymer, wherein the mixer has an energy dissipation rate of approximately $10^4$-$10^5$ W/kg of mixed solvents during the mixing process, thereby producing a collection of roughly spherical nanoparticles having an average particle diameter of about 50 nm to about 200 nm and a polydispersity index of less than 0.3 by flash nanoprecipitation;

and said drying comprises:

removing most of the organic solvent by dialysis; and co-freeze drying the nanoparticles with a cryoprotectant at a concentration of not more than 2% w/v, wherein the cryoprotectant is selected from the group consisting of a sugar and a beta-cyclodextrin;

thereby yielding a solid powder.

7. The collection of solid nanoparticles of claim 1, wherein the collection is present in the form of a solid powder, and the solid powder can be readily dispersed in water with a minimum change in particle size and a minimum change in particle morphology.

8. The collection of solid nanoparticles of claim 1, wherein the drug molecule has a Log P value of from about 3 to about 6.

9. The collection of solid nanoparticles of claim 8, wherein the drug molecule has a Log P value of from about 3 to about 5.

10. The collection of solid nanoparticles of claim 9, wherein the drug molecule has a Log P value of from about 3 to about 4.

11. The collection of solid nanoparticles of claim 1, wherein the amphiphilic diblock copolymer has a molecular weight of from about 2,000 to about 10,000 g/mol.

12. The collection of solid nanoparticles of claim 11, wherein the amphiphilic diblock copolymer comprises polyethylene glycol-polylactic acid (PEG-PLA).

13. The collection of solid nanoparticles of claim 1, wherein each nanoparticle further comprises a surfactant selected from the group consisting of lecithin, cholesterol, and D-α-Tocopherol polyethylene glycol 1000 succinate.

14. The collection of solid nanoparticles of claim 1, wherein the nanoparticles are on average characterized by a change of particle size of not more than 40% after a storage time of at least 1 day.

15. The collection of solid nanoparticles of claim 14, wherein the nanoparticles are on average characterized by a change of particle size of not more than 40% after a storage time of at least 1 week.

16. The collection of solid nanoparticles of claim 15, wherein the nanoparticles are on average characterized by a change of particle size of not more than 40% after a storage time of at least 1 month.

17. The method of claim 6, wherein the pharmaceutically-acceptable hydrophilic polymer is present during mixing at a concentration of at least about 0.5% w/v.

18. The method of claim 6, wherein the organic solvent comprises an amphiphilic diblock copolymer.

19. The collection of solid nanoparticles of claim 7, wherein the mean particle size is increased by not more than 20 nm upon dispersing the solid powder into water.

20. The collection of solid nanoparticles of claim 7, wherein the mean particle size is increased by not more than 30% upon dispersing the solid powder into water.

21. The method of claim 6, wherein said mixing occurs over a time period of less than a second.

22. The method of claim 21, wherein said mixing occurs over a time period of a few milliseconds.

23. The method of claim 6, wherein the organic solvent is water-miscible.

24. The method of claim 23, wherein the organic solvent comprises acetone, tetrahydrofuran, or dimethylformamide.

25. The collection of solid nanoparticles of claim 9, wherein the drug molecule has a Log P value of from about 4 to about 5.

26. The collection of solid nanoparticles of claim 8, wherein the drug molecule has a Log P value of from about 4 to about 6.

27. The collection of solid nanoparticles of claim 26, wherein the drug molecule has a Log P value of from about 5 to about 6.

28. A method of making the collection of solid nanoparticles of claim 1, the method comprising: mixing in a mixer an organic solvent, an antisolvent, a molecule having a Log P value of about 3 or above, and a pharmaceutically-acceptable hydrophilic polymer, wherein the mixer has an energy dissipation rate of approximately $10^4$-$10^5$ W/kg of mixed solvents during the mixing process, thereby producing a collection of roughly spherical nanoparticles.

* * * * *